United States Patent
Adams et al.

(10) Patent No.: US 6,610,695 B1
(45) Date of Patent: Aug. 26, 2003

(54) ARYLOXY SUBSTITUTED PYRIMIDINE IMIDAZOLE COMPOUNDS

(75) Inventors: Jerry L. Adams, Wayne, PA (US); Dennis Lee, Foster City, CA (US); Scott A. Long, Ballwin, MO (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/445,652

(22) PCT Filed: Jun. 19, 1998

(86) PCT No.: PCT/US98/12828

§ 371 (c)(1), (2), (4) Date: Mar. 22, 2001

(87) PCT Pub. No.: WO98/57966

PCT Pub. Date: Dec. 23, 1998

Related U.S. Application Data

(60) Provisional application No. 60/050,224, filed on Jun. 19, 1997.

(51) Int. Cl.[7] .................. A61K 31/506; C07D 403/04
(52) U.S. Cl. ................... 514/256; 514/269; 514/274; 514/275; 544/298; 544/316; 544/319; 544/322; 544/328; 544/331
(58) Field of Search ................ 544/298, 316, 544/319, 322, 328, 331; 514/256, 269, 274, 275

(56) References Cited

U.S. PATENT DOCUMENTS

| | | | |
|---|---|---|---|
| 3,707,475 A | 12/1972 | Lombardino | 260/309 |
| 3,772,441 A | 11/1973 | Lombardino | 424/273 |
| 3,929,807 A | 12/1975 | Fitzi | 260/294.8 R |
| 3,940,486 A | 2/1976 | Fitzi | 424/263 |
| 4,058,614 A | 11/1977 | Baldwin | 424/263 |
| 4,199,592 A | 4/1980 | Cherkofsky | 424/273 |
| 4,447,431 A | 5/1984 | Sallmann | 424/246 |
| 4,503,065 A | 3/1985 | Wilkerson | 514/396 |
| 4,565,875 A | 1/1986 | Cavender | 548/336 |
| 4,686,231 A | 8/1987 | Bender et al. | 514/333 |
| 4,822,805 A | 4/1989 | Tasasugi et al. | 514/341 |
| 5,559,137 A | 9/1996 | Adams et al. | 514/341 |
| 5,593,991 A | 1/1997 | Adams et al. | 514/235.2 |
| 5,593,992 A | 1/1997 | Adams et al. | 514/235.8 |
| 5,656,644 A | 8/1997 | Adams et al. | 514/341 |
| 5,658,903 A | 8/1997 | Adams et al. | 514/235.8 |
| 5,663,334 A | 9/1997 | Sheldrake et al. | 544/122 |
| 5,670,527 A | 9/1997 | Adams et al. | 514/341 |
| 5,686,455 A | 11/1997 | Adams et al. | 514/256 |
| 5,716,955 A | 2/1998 | Adams et al. | 514/235.8 |
| 5,716,972 A | 2/1998 | Adams et al. | 514/314 |
| 5,739,143 A | 4/1998 | Adams et al. | 514/275 |
| 5,756,499 A | 5/1998 | Adams et al. | 514/235.8 |
| 5,777,097 A | 7/1998 | Lee et al. | 536/24.31 |
| 5,783,664 A | 7/1998 | Lee et al. | 530/350 |
| 5,811,549 A | 9/1998 | Adams et al. | 544/123 |
| 5,864,036 A | 1/1999 | Adams et al. | 544/123 |
| 5,869,043 A | 2/1999 | McDonnell et al. | 424/94.1 |
| 5,869,660 A | 2/1999 | Adams et al. | 544/122 |
| 5,871,934 A | 2/1999 | Lee et al. | 435/7.1 |
| 5,916,891 A | 6/1999 | Adams et al. | 514/256 |
| 5,917,043 A | 6/1999 | Sisko | 544/332 |
| 5,929,076 A | 7/1999 | Adams et al. | 514/252 |
| 5,955,366 A | 9/1999 | Lee et al. | 435/471 |
| 5,969,184 A | 10/1999 | Adams et al. | 564/154 |
| 5,977,103 A | 11/1999 | Adams et al. | 514/235.2 |
| 5,998,425 A | 12/1999 | Adams et al. | 514/275 |
| 6,008,235 A | 12/1999 | Adams et al. | 514/333 |
| 6,268,370 B1 * | 7/2001 | Adams et al. | 514/256 |

FOREIGN PATENT DOCUMENTS

| | | |
|---|---|---|
| WO | WO 92/10190 | 6/1992 |
| WO | WO 92/10498 | 6/1992 |
| WO | WO 95/02591 | 1/1995 |
| WO | WO 95/03297 | 2/1995 |
| WO | WO 95/13067 | 5/1995 |
| WO | WO 95/31451 | 11/1995 |
| WO | WO 96/21452 | 7/1996 |
| WO | WO 96/21654 | 7/1996 |
| WO | WO 96/40143 | 12/1996 |
| WO | WO 97/12876 | 4/1997 |
| WO | WO 97/23479 | 7/1997 |
| WO | WO 97/25045 | 7/1997 |
| WO | WO 97/25046 | 7/1997 |
| WO | WO 97/25047 | 7/1997 |
| WO | WO 97/25048 | 7/1997 |
| WO | WO 97/32583 | 9/1997 |
| WO | WO 97/33883 | 9/1997 |
| WO | WO 97/35855 | 10/1997 |

(List continued on next page.)

OTHER PUBLICATIONS

Adams et al., Chemical Abstracts, vol. 122:265375, 1995.*
Armarego, W. J. Chem. Soc., (JCSOA9) p. 561 (1962).
Becker et al., J. Immunol., 147, p. 4307 (1991).
Colotta et al., J. Immunol., 132(2), p. 936 (1984).
Dinarello et al., Rev.Infect.Disease, 6, p. 51 (1984).
Dinarello, J.Clin.Immun., 5(5), p. 287–297 (1985).
Engel & Steglich, Liebigs Ann. Chem., 1916 (1978).
Fischer et al., Rec.Trav.Chim.Pays.Bas., 84, p. 439 (1965).
Garigipati, R., Tetrahedron Letters, 31, p. 190 (1989).
Gilbert, Synthesis, pp.30–32 (1972).
Ishibashi, Chem. Pharm. Bull., 37(8), pp.2214–2216 (1989).
Johnson, P.A., J.Chem.Soc., Perkin Trans., vol. 1, pp. 895–905 (1996).
Katritzky, Synthesis, pp. 45–47 (1993).
Kawasaki et al., J. Bio. Chem., 272(30), pp. 18518–18521.
Kumada et al., Tetrahedron Letters, 22, p. 5319 (1981).

(List continued on next page.)

Primary Examiner—Richard L. Raymond
(74) Attorney, Agent, or Firm—Dara L. Dinner; Theodore R. Furman; Charles M. Kinzig

(57) ABSTRACT

Novel 2,4,5-triaryl substituted imidazole compounds and compositions for use in therapy of CSBP/RK/p38 mediated diseases.

22 Claims, 2 Drawing Sheets

FOREIGN PATENT DOCUMENTS

| | | |
|---|---|---|
| WO | WO 97/35856 | 10/1997 |
| WO | WO 97/36587 | 10/1997 |
| WO | WO 97/47618 | 12/1997 |
| WO | WO 98/07425 | 2/1998 |
| WO | WO 98/16230 | 4/1998 |
| WO | WO 98/22109 | 5/1998 |
| WO | WO 98/25619 | 6/1998 |
| WO | WO 98/47892 | 10/1998 |
| WO | WO 98/57966 | 12/1998 |
| WO | WO 99/01130 | 1/1999 |
| WO | WO 99/01131 | 1/1999 |
| WO | WO 99/01136 | 1/1999 |
| WO | WO 99/01452 | 1/1999 |
| WO | WO 99/17776 | 4/1999 |
| WO | WO 99/18942 | 4/1999 |
| WO | WO 99/32121 | 7/1999 |
| WO | WO 99/61437 | 12/1999 |
| WO | WO 99/61440 | 12/1999 |

OTHER PUBLICATIONS

Morton et al., Tetrahedron Letters, 4123 (1982).
Poli et al., Proc.Nat'l Acad.Sci., 87, p. 782–784 (1990).
Pridgen, J.Org.Chem., 47, p. 4319 (1982).
R.P.Soni, Aust.J.Chem., 35, p. 1493–1496 (1982).
Simon et al., J. Immunol. Methods, 84, p. 85 (1985).
Snieckus, V., Tetrahedron Letters, 29, 2135 (1988).
Stille, J.Amer.Chem.Soc., 109, p. 5478 (1978).
Strzybny et al., J. Org. Chem., 28, p. 3381 (1963).
Terashimia, M., Chem.Pharm.Bull., 11, p. 4755 (1985).
Thompson, W.J., et al., J.Org.Chem., 49, p.5237 (1984).
Uno, Bull. Chem. Soc. Japan., vol. 69, pp. 1763–1767 (1996).
VanLeusen et al., J.O.C., 42, p. 1153 (1977).
Zavyalov, et al., Khim Farm Zh, 26(3), p. 88 (1992) (With Translation).

* cited by examiner

ARYLOXY SUBSTITUTED PYRIMIDINE IMIDAZOLE COMPOUNDS

This application claims the benefit of 60/050,224 filed Jun. 19, 1997.

FIELD OF THE INVENTION

This invention relates to a novel group of aryloxypyrimidine substituted imidazole compounds, processes for the preparation thereof, the use thereof in treating cytokine mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter. T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2. and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al., Science 265, 808(1994)) identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee, et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low mM range [Lee, et al., Int. J. Immunopharmac. 10(7), 835(1988)] and exhibited activity in animal models which are refractory to cyclooxygenase inhibitors [Lee, et al., Annals N. Y. Acad. Sci., 696, 149 (1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. Trends Cell Biol., 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic B cells [review of the biological activities which have been attributed to IL-1 Dinarello, J. Clinical Immunology, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL- 1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD 18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al., *Pharmacol. Comm.* 7, 323–229 (1996)].

There remains a need for treatment in this field, for compounds which are cytokine suppressive anti-inflammatory drugs, i.e. compounds which are capable of inhibiting the CSBP/p38/RK kinase.

SUMMARY OF THE INVENTION

Figure 1:
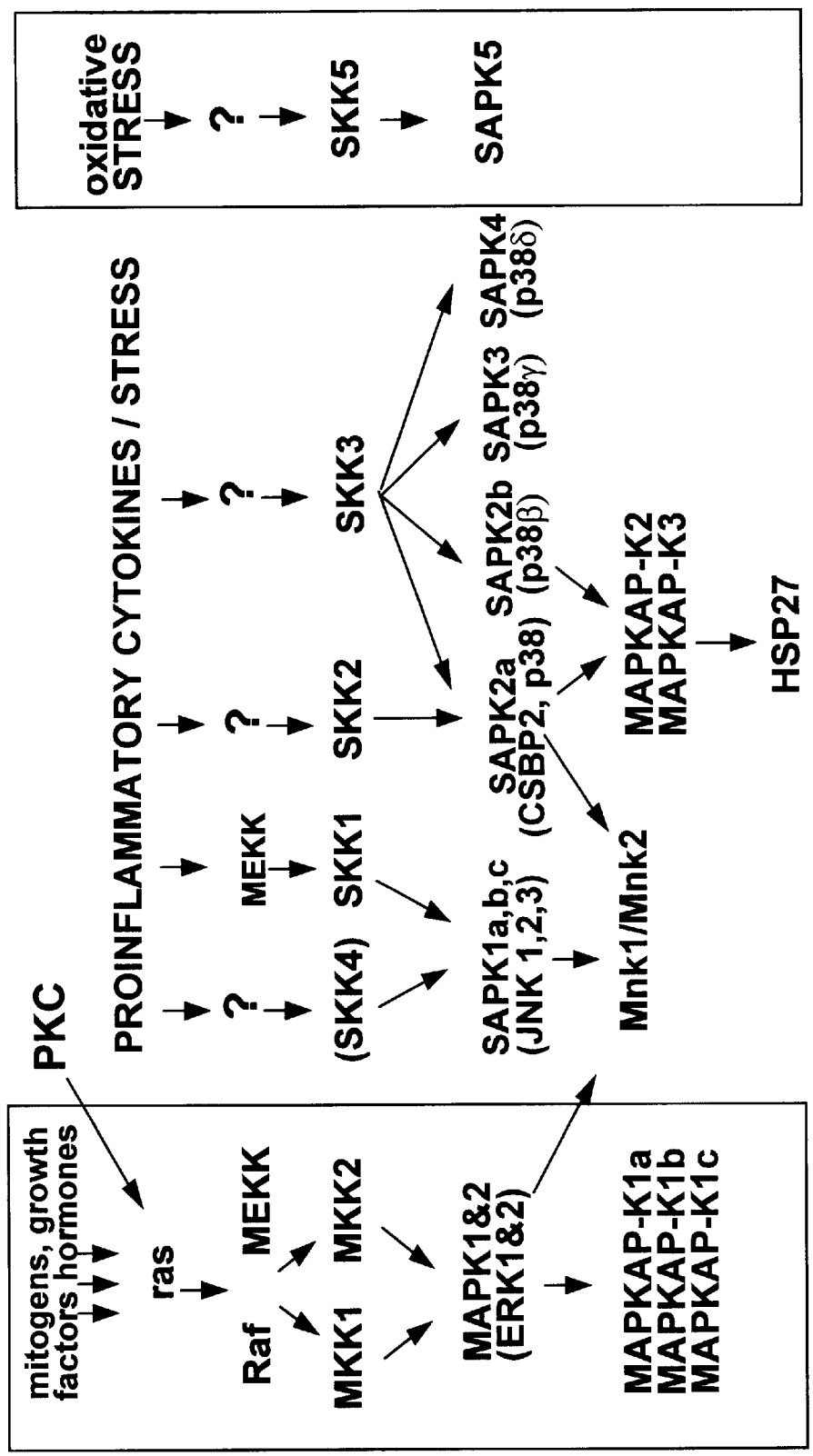
FIG. 1 demonstrates the mitogen-activated protein kinase (MAP) kinase cascade.
Figure 2:
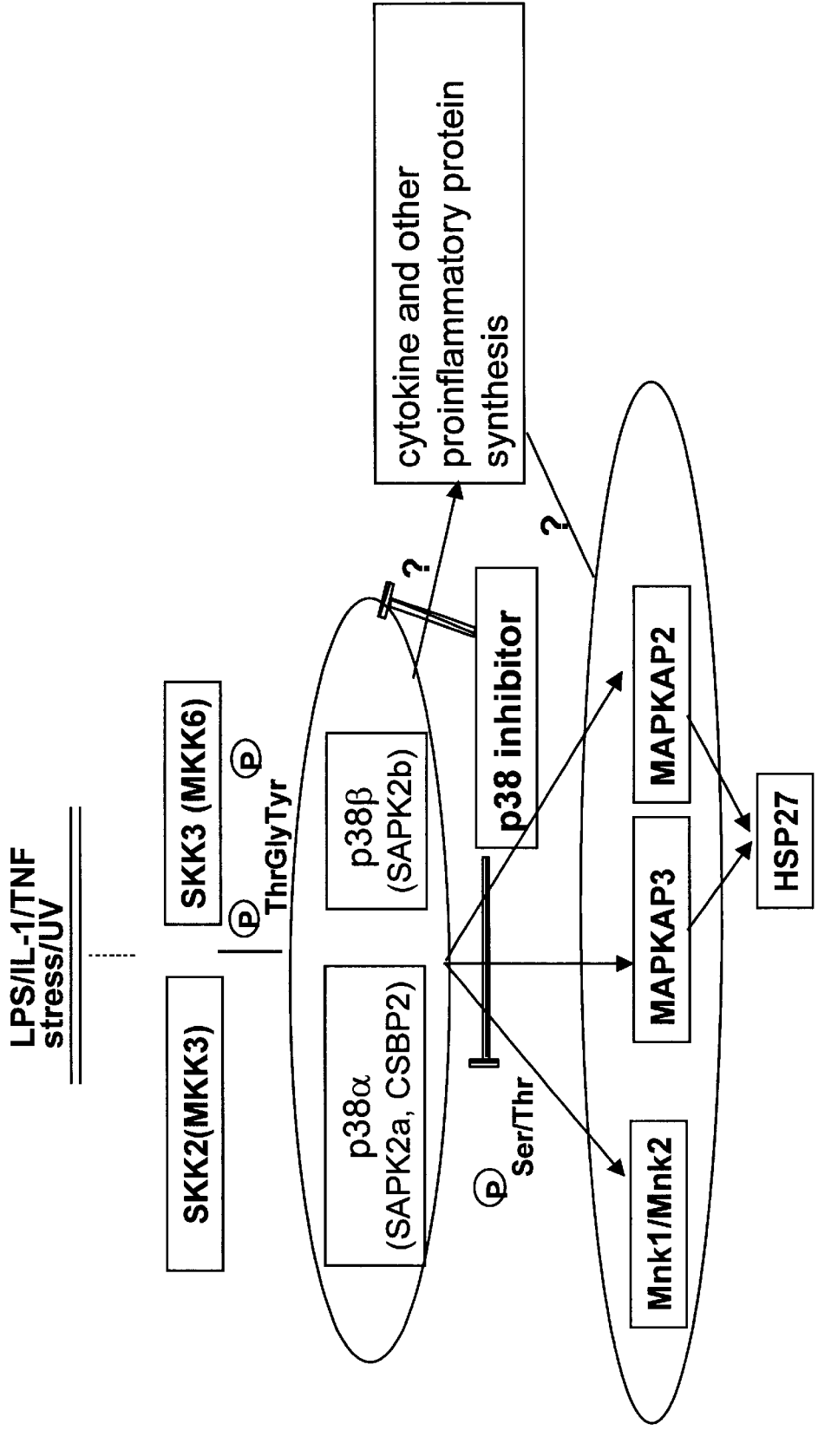
FIG. 2 demonstrates the p38 kinase pathway.

This invention relates to the novel compounds of Formula (I) and pharmaceutical compositions comprising a compound of Formula (I) and a pharmaceutically acceptable diluent or carrier.

This invention relates to a method of propylaxis, or the treatment of a CSBP/RK/p38 kinase mediated disease in a mammal in need thereof, which method comprises administering to said mammal an effective prophylatic or treatment amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-6 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of formula (I):

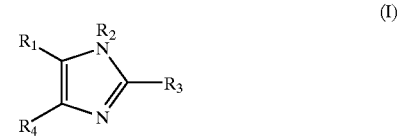

wherein:

$R_1$ is 4-pyrimidinyl ring which ring is substituted by Y, or $NHR_a$, and is optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is $X_1-R_a$;

$X_1$ is sulfur or oxygen;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_2$ is hydrogen, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, aryl, aryl$C_{1-10}$ alkyl, heteroaryl, heteroaryl $C_{1-10}$ alkyl, heterocyclyl, heterocyclyl$C_{1-10}$ alkyl, $(CR_{10}R_{28})_nOR_{12}$, $(CR_{10}R_{28})_n'OR_{13}$, $(CR_{10}R_{28})n'S(O)_mR_{25}$, $(CR_{10}R_{28})_nS(O)_2R_{25}$, $(CR_{10}R_{28})_n'NHS(O)_2R_{25}$, $(CR_{10}R_{28})_n'NR_8R_9$, $(CR_{10}R_{28})_n'NO_2$, $(CR_{10}R_{28})_n'CN$, $(CR_{10}R_{28})_n'S(O)_mNR_8R_9$, $(CR_{10}R_{28})_n'C(Z)R_{13}$, $(CR_{10}R_{28})_n'C(Z)OR_{13}$, $(CR_{10}R_{28})_n'C(Z)NR_8R_9$, $(CR_{10}R_{28})_n'C(Z)NR_{13}OR_{12}$, $(CR_{10}R_{28})_n'NR_{10}C(Z)R_{13}$, $(CR_{10}R_{28})_n'NR_{10}C(Z)NR_8R_9$, $(CR_{10}R_{28})_n'N(OR_{21})C(Z)NR_8R_9$, $(CR_{10}R_{28})_n'N(OR_{21})C(Z)R_{13}$, $(CR_{10}R_{28})_n'C(=NOR_{21})R_{13}$, $(CR_{10}R_{28})_n'NR_{10}C(=NR_{27})NR_8R_9$, $(CR_{10}R_{28})_n{'}OC(Z)NR_8R_9$, $(CR_{10}R_{28})_n{'}NR_{10}C(Z)OR_{10}$, $(CR_{10}R_{28})_n{'}NR_{10}C(Z)OR_{10}$, 5-$(R_{25})$-1,2,4-oxadizaol-3-yl or 4-$(R_{12})$-5-$(R_{18}R_{19})$-4,5-dihydro-1,2,4-oxadiazol-3-yl;wherein the cyclcoalkyl, cycloalkyl alkyl, aryl, arylalkyl, heteroaryl, heteroarylalkyl, heterocyclyl, or heterocyclylalkyl moieties may be optionally substituted;

n is 0 or an integer from 1 to 10;

n' is an integer having a value of 1 to 10;

m is 0, or the integer 1 or 2;

m' is an integer having a value of 1 or 2, m" is 0, or an integer having a value of 1 to 5;

t is a number having a value of 1, 2 or 3;

v is 0, or an integer having a value of 1 or 2;

$R_3$ is Q—$(Y_1)_t$;

Q is an aryl or heteroaryl group;

Z is oxygen or sulfur;

$Y_1$ is independently selected from hydrogen, $C_{1-5}$ alkyl, halo-substituted $C_{1-5}$ alkyl, halogen, or $(CR_{10}R_{20})_nY_2$;

$Y_2$ is $OR_8$, $NO_2$, $S(O)_m{''}R_{11}$, $SR_8$, $S(O)_m{''}OR_8$, $S(O)_mNR_8R_9$, $NR_8R_9$, $O(CR_{10}R_{20})_n{'}NR_8R_9$, $C(O)R_8$, $CO_2R_8$, $CO_2(CR_{10}R_{20})_n{'}CONR_8R_9$, $ZC(O)R_8$, $CN$, $C(Z)NR_8R_9$, $NR_{10}C(Z)R_8$, $C(Z)NR_8OR_9$, $NR_{10}C(Z)NR_8R_9$, $NR_{10}S(O)_m{''}R_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR_{13})ZR_{11}$, $OC(Z)NR_8R_9$, $NR_{10}S(O)_m{''}CF_3$, $NR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, nitro, cyano, $C(Z)NR_7R_{17}$, $C(Z)OR_{23}$, $(CR_{10}R_{20})_vCOR_{36}$, $SR_5$, $SOR_5$, $OR_{36}$, halo-substituted-$C_{1-4}$ alkyl, $C_{1-4}$ alkyl, $ZC(Z)R_{36}$, $NR_{10}C(Z)R_{23}$, or $(CR_{10}R_{20})_vNR_{10}R_{20}$ and which, for other positions of substitution, is halo, nitro, cyano, $C(Z)NR_{16}R_{26}$, $C(Z)OR_8$, $(CR_{10}R_{20})_m{''}COR_8$, $S(O)_mR_8$, $OR_8$, halo-substituted-$C_{1-4}$ alkyl, $C_{1-4}$ alkyl, $CR_{10}R_{20})_m{''}$—$NR_{10}C(Z)R_8$, $NR_{10}S(O)_m{'}R_{11}$, $NR_{10}S(O)_m{'}NR_7R_{17}$, $ZC(Z)R_8$ or $(CR_{10}R_{20})_m{''}NR_{16}R_{26}$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ hydrogen, heterocyclyl, heterocyclylalkyl or $R_{11}$;

$R_9$ is hydrogen $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, —$C(Z)R_{13}$ or optionally substituted $C_{1-4}$ alkyl, optionally substituted aryl, optionally substituted aryl$C_{1-4}$ alkyl, or $S(O)_2R_{25}$;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl, wherein all of these moieties may be optionally substituted;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{18}$ and $R_{19}$ is each independently selected from hydrogen, $C_{1-4}$ alkyl, substituted alkyl, optionally substituted aryl, optionally substituted arylalkyl or together denote a oxygen or sulfur;

$R_{21}$ is hydrogen, a pharmaceutically acceptable cation, $C_{1-10}$ alkyl, $C_{3-7}$ cycloalkyl, aryl, aryl $C_{1-4}$ alkyl, heteroaryl, heteroarylalkyl, heterocyclyl, aroyl, or $C_{1-10}$ alkanoyl;

$R_{22}$ is $R_{10}$ or $C(Z)$—$C_{1-4}$ alkyl;

$R_{23}$ is $C_{1-4}$ alkyl, halo-substituted-$C_{1-4}$ alkyl, or $C_{3-5}$ cycloalkyl;

$R_{25}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{27}$ is hydrogen, cyano, $C_{1-4}$ alkyl, $C_{3-7}$ cycloalkyl, or aryl;

$R_{28}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

$R_{36}$ is hydrogen or $R_{23}$;

or a pharmaceutically acceptable salt thereof.

DETAILED DESCRIPTION OF THE INVENTION

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retovirus infections, such as but not limited to feline immunodeficiency virus (FIV), bovine immunodeficiency virus, or canine immunodeficiency virus or other retroviral infections.

In compounds of Formula (I), $R_1$ is a 4-pyrimidinyl ring, which ring is substituted by Y, or $NHR_a$. The ring may also be optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$alkylsulfinyl, $CH_2OR_{12}$, amino, mono and di-$C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$. Preferably, the ring is substituted by Y.

Suitably, Y is $X_1$–$R_a$; and $X_1$ is sulfur or oxygen, preferably oxygen.

Suitably, $R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted. Preferably $R_a$ is $C_{1-6}$alkyl, aryl, or aryl$C_{1-6}$alkyl. More preferably aryl, or aryl$C_{1-6}$alkyl.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; wherein each of these moieties may be optionally substituted.

Suitably, $R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; wherein each of these moieties may be optionally substituted.

A preferred ring placement on the 4-pyrimidinyl ring is at the 2-position, such as in 2-methoxy-pyrimidine or 2-phenxoy-pyrimidine.

Suitably, $R_2$ is hydrogen, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$alkyl, $C_{5-7}$ cycloalkenyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{28})_n$ $OR_{12}$, $(CR_{10}R_{28})_n'OR_{13}$, $(CR_{10}R_{28})_n'S(O)_mR_{25}$, $(CR_{10}R_{28})_n$ $S(O)_2R_{25}$, $(CR_{10}R_{28})_n'NHS(O)_2R_{25}$, $(CR_{10}R_{28})_n'NR_8R_9$, $(CR_{10}R_{28})_n'NO_2$, $(CR_{10}R_{28})_n'CN$, $(CR_{10}R_{28})_n'S(O)_mNR_8R_9$, $(CR_{10}R_{28})_n'C(Z)R_{13}$, $(CR_{10}R_{28})_n'C(Z)OR_{13}$, $(CR_{10}R_{28})_n'C(Z)NR_8R_9$, $(CR_{10}R_{28})_n'C(Z)NR_{13}OR_{12}$, $(CR_{10}R_{28})_n'NR_{10}C(Z)R_{13}$, $(CR_{10}R_{28})_n'NR_{10}C(Z)NR_8R_9$, $(CR_{10}R_{28})_n'N(OR_{21})C(Z)NR_8R_9$, $(CR_{10}R_{28})_n'N(OR_{21})C(Z)R_{13}$, $(CR_{10}R_{28})_n'C(=NOR_{21})R_{13}$, $(CR_{10}R_{28})_n'NR_{10}C(=NR_{27})NR_8R_9$, $(CR_{10}R_{28})_n'OC(Z)NR_8R_9$, $(CR_{10}R_{28})_n'NR_{10}C(Z)OR_{10}$, $(CR_{10}R_{28})_n NR_{10}C(Z)OR_{10}$, 5-$(R_{25})$-1,2,4-oxadizaol-3-yl or 4-$(R_{12})$-5-$(R_{18}R_{19})$-4,5-dihydro-1,2,4-oxadiazol-3-yl;wherein the cyclcoalkyl, cycloalkyl alkyl, aryl, arylalkyl, heteroaryl, heteroarylalkyl, heterocyclyl, or heterocyclylalkyl moieties may be optionally substituted.

Preferably $R_2$ is hydrogen, an optionally substituted heterocyclyl ring, and optionally substituted heterocyclyl$C_{1-10}$ alkyl, an optionally substituted $C_{1-10}$ alkyl, an optionally substituted $C_{3-7}$ cycloalkyl, an optionally substituted $C_{3-7}$cycloalkyl $C_{1-10}$ alkyl, $(CR_{10}R_{28})_nOR_{12}$, $(CR_{10}R_{28})_n'C(Z)OR_{13}$ group, $(CR_{10}R_{28})_n'NR_8R_9$, $(CR_{10}R_{28})_n'NHS(O)_2R_{25}$, $(CR_{10}R_{28})_n'S(O)_mR_{25}$, an optionally substituted aryl; an optionally substituted aryl$C_{1-10}$ alkyl, $(CR_{10}R_{28})_n'OR_{13}$, $(CR_{10}R_{28})_n'C(Z)R_{13}$, or $(CR_{10}R_{28})_n'C(=NOR_{21})R_{13}$.

More preferably $R_2$ is hydrogen, $(CR_{10}R_{28})_nOR_{12}$, an optionally substituted $C_{1-10}$ alkyl, an optionally substituted heterocyclyl ring, an optionally substituted heterocyclyl$C_{1-10}$ alkyl, an optionally substituted aryl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_n'NR_8R_9$, or $(CR_{10}R_{20})_n'C(Z)OR_{13}$ group. Another prefered grouping for $R_2$ is hydrogen, an optionally substituted heterocyclyl ring, an optionally substituted heterocyclyl$C_{1-10}$ alkyl, an optionally substituted $C_{3-7}$ cycloalkyl, or an optionally substituted $C_{3-7}$cycloalkyl $C_{1-10}$ alkyl.

When $R_2$ is an optionally substituted heterocyclyl the ring is preferably a morpholino, pyrrolidinyl, or a piperidinyl group. When the ring is optionally substituted the substituents may be directly attached to the free nitrogen, such as in the piperidinyl group or pyrrole ring, or on the ring itself. Preferably the ring is a piperidine or pyrrole, more preferably piperidine. heterocyclyl ring may be optionally substituted one to four times independently by halogen; $C_{1-4}$ alkyl; aryl, such as phenyl; aryl alkyl, such as benzyl—wherein the aryl or aryl alkyl moieties themselves may be optionally substituted (as in the definition section below); $C(O)OR_{13}$, such as the $C(O)C_{1-4}$ alkyl or $C(O)OH$ moieties; $C(O)H$; $C(O)C_{1-4}$ alkyl, hydroxy substituted $C_{1-4}$ alkyl, $C_{1-4}$ alkoxy, $S(O)_mC_{1-4}$ alkyl (wherein m is 0, 1, or 2), $NR_{10}R_{20}$ (wherein $R_{10}$ and $R_{20}$ are independently hydrogen or $C_{1-4}$alkyl).

Preferably if the ring is a piperidine, the ring is attached to the imidazole at the 4-position, and the substituents are directly on the available nitrogen, i.e. a 1-Formyl4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2 or 6 position or both, such as 2,2,6,6-tetramethyl4-piperidine. Similarly, if the ring is a pyrrole, the ring is attached to the imidazole at the 3-position, and the substituents are also directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrollidinyl propyl, and piperidinyl propyl moieties. The heterocyclic ring herein is also optionally substituted in a similar manner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_5$ to $C_6$ ring.

The $C_{3-7}$ cycloalkyl, and $C_{3-7}$ cycloalkyl $C_{1-10}$ alkyl ring may be optionally substituted one or more times independently by halogen, such as fluorine, chlorine, bromine or iodine; hydroxy; $C_{1-10}$ alkoxy, such as methoxy or ethoxy; $S(O)_m$ alkyl, wherein m is 0, 1, or 2, such as methyl thio, methylsulfinyl or methyl sulfonyl; amino, mono & di-substituted amino, such as in the $NR_7R_{17}$ group; or where the $R_7R_{17}$ may cyclize together with the nitrogen to which they are attached to form a 5 to 7 membered ring which optionally includes an additional heteroatom selected from O/N/S; $C_{1-10}$ alkyl, such as methyl, ethyl, propyl, isopropyl, or t-butyl; halosubstituted alkyl, such as $CF_3$; hydroxy substituted $C_{1-10}$ alkyl; $C(O)OR_{13}$, such as the free acid or methyl ester derivative; an optionally substituted aryl, such as phenyl; an optionally substituted arylalkyl, such as benzyl or phenethyl; and further where these aryl or aryl alkyl moieties may also be substituted one to two times by halogen; hydroxy; $C_{1-10}$ alkoxy; $S(O)_m$ alkyl; amino, mono & di-substituted amino, such as in the $NR_7R_{17}$ group; alkyl or halosubstituted alkyl.

When $R_2$ is $(CR_{10}R_{28})_n'NR_8R_9$, $R_8$ and $R_9$ are as defined in Formula (I), preferably $R_8$ and $R_9$ are each independently selected from hydrogen, optionally substituted $C_{1-4}$ alkyl, optionally substituted aryl or an optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$. It is recognized that in some instances this can yield the same moiety as a heterocyclic $C_{1-10}$ alkyl moiety noted above which is also a suitable $R_2$ variable. Preferably $R_8$ and $R_9$ are independently hydrogen, $C_{1-4}$ alkyl, preferably methyl, or benzyl. The n term is preferably 1 to 4, more preferably 3 or 4, and most preferably 3, such as in a propyl group. Preferred groups include, but are not limited to, aminopropyl, (N-methyl-N-benzyl) aminopropyl, (N-Phenyl-methyl)amino-1-propyl, or diethylamino propyl.

When $R_2$ is a $(CR_{10}R_{28})_n'C(Z)OR_{13}$ group, $R_{13}$ is suitably hydrogen, $C_{1-4}$ alkyl, especially methyl. The n' term is preferably 1 to 4, more preferably 2 or 3, such as in an ethyl or propyl group. Preferred groups include, but are not limited to, carboxymethyl-1-butyl, carboxy-1-propyl, or 2-acetoxyethyl.

When $R_2$ is a $(CR_{10}R_{28})_n'S(O)_mR_{25}$ group m is 0, 1, or 2, and R18 is preferably aryl, especially phenyl, or $C_{1-10}$ alkyl, especially methyl. The n term is preferably 1 to 4, more preferably 2 or 3, such as in an ethyl or propyl group.

When $R_2$ is a $(CR_{10}R_{28})_n'OR_{13}$ group, $R_{13}$ is suitably hydrogen, aryl, especially phenyl, or $C_{1-10}$ alkyl, especially methyl or ethyl. The n term is preferably 1 to 4, more preferably 2 or 3, such as in an ethyl or propyl group.

When $R_2$ is a $(CR_{10}R_{28})_n'NHS(O)_2R_{25}$ group, $R_{25}$ is suitably alkyl, especially methyl. The n term is preferably 1 to 4, more preferably 2 or 3, such as in an ethyl or propyl group.

When $R_2$ is a optionally substituted aryl, the aryl is preferably phenyl. The aryl ring may be optionally substituted one or more times, preferably by one or two substituents, independently selected from $C_{1-4}$ alkyl, halogen, especially fluoro or chloro, $(CR_{10}R_{28})_tOR_{13}$, (wherein t is 0, or an integer of 1 to 4), $(CR_{10}R_{28})_tNR_{10}R_{20}$, especially amino or mono- or di-alkylamino $(CR_{10}R_{28})_tS(O)_mR_{25}$, wherein m is 0, 1 or 2; SH, $(CR_{10}R_{20})_nNR_8R_9$, $NR_{10}C(Z)R_8$ (such $NHCO(C_{1-10}$ alkyl)), or $NR_{10}S(O)_mR_{25}$ (such as $NHSO_2(C_{1-10}$ alkyl)). Preferably the phenyl is substituted in the 3 or 4- position by $(CR_{10}R_{28})_tS(O)_mR_{25}$, and $R_{25}$ is preferably $C_{1-10}$ alkyl, especially methyl.

When $R_2$ is an optionally substituted heteroaryl or heteroarylalkyl group the ring may be optionally substituted one or more times, preferably by one or two substituents, independently selected from one or more times, by $C_{1-4}$ alkyl, halogen, especially fluoro or chloro, $(CR_{10}R_{28})_tOR_{13}$, $(CR_{10}R_{28})_tNR_{10}R_{20}$, especially amino or mono- or di-alkylamino, $(CR_{10}R_{28})_tS(O)_mR_{25}$, wherein m is 0, 1 or 2; SH, $(CR_{10}R_{28})_n—NR_8R_9$, $NR_{10}C(Z)R_8$ (such $NHCO(C_{1-10}$ alkyl)); $NR_{10}S(O)_mR_{25}$ (such as $NHSO_2(C_{1-10}$ alkyl)); t is 0, or an integer of 1 to 4.

One skilled in the art would readily recognize that when $R_2$ is a $(CR_{10}R_{28})_nOC(Z)R_{13}$, or $(CR_{10}R_{28})_nOC(Z)NR_8R_9$ moiety, or any similarly substituted group that n is preferably at least 2 which will allow for the synthesis of stable compounds.

Preferably $R_2$ is hydrogen, $C_{1-4}$ alkyl (branched and unbranched), a methylthio propyl, a methylsulfinyl propyl, an amino propyl, N-methyl-N-benzylamino propyl group, diethylamino propyl, cyclopropyl methyl, morpholinyl butyl, morpholinyl propyl, a morpholinyl ethyl, a piperidine or a substituted piperidine. More preferably $R_2$ is isopropyl; butyl; t-butyl; n-propyl; methylthiopropyl or methylsulfinyl propyl; morpholino propyl; morpholinyl butyl; phenyl substituted by halogen, thioalkyl or sulfinyl alkyl such as a methylthio, methylsulfinyl or methylsulfonyl moiety; piperidinyl; 1-Formyl-4-piperidine; 1-benzyl-4-piperidine; 1-methyl-4-piperidine, or a 1-ethoxycarbonyl-4-piperidine.

Suitably, $R_3$ is Q-$(Y_1)_t$, and Q is an optionally substituted aryl or heteroaryl moiety. Preferably, when Q is an aryl, it is phenyl, and when Q is a heteroaryl, preferred rings include thienyl, pyrrole, pyridine, or pyrimidine. More preferably, Q is a substituted phenyl. Preferably when t is 1 and $R_3$ is mono-substituted phenyl, the substituent is located at the 4-position of the ring.

Suitably, t is a number having a value of 1 to 3, preferably t is 1 or 2.

Suitably $Y_1$ is independently selected from hydrogen, $C_{1-5}$ alkyl, halo-substituted $C_{1-5}$ alkyl, halogen, or $(CR_{10}R_{20})_nY_2$.

Suitably, $Y_2$ is $OR_8$, $NO_2$, $S(O)_m''R_{11}$, $SR_8$, $S(O)_m''OR_8$, $S(O)_mNR_8R_9$, $NR_8R_9$, $O(CR_{10}R_{20})_n'NR_8R_9$, $C(O)R_8$, $CO_2R_8$, $CO_2(CR_{10}R_{20})_n'CONR_8R_9$, $ZC(O)R_8$, CN, $C(Z)NR_8R_9$, $NR_{10}C(Z)R_8$, $C(Z)NR_8OR_9$, $NR_{10}C(Z)NR_8R_9$, $NR_{10}S(O)_m''R_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR_{13})ZR_{11}$, $OC(Z)NR_8R_9$, $NR_{10}S(O)_m''CF_3$, $NR_{10}C(Z)OR_{10}$, 5-$(R_{18})$-1,2,4-oxadiazol-3-yl or 4-$(R_{12})$-5-$(R_{18}R_{19})$-4,5-dihydro-1,2,4-oxadiazol-3-yl.

Preferably when Q is substituted by 1 or 2 substituents, those substituents include halogen, $C_{1-5}$ alkyl and $(CR_{10}R_{20})_nY_2$. The $Y_2$ are preferably $OR_8$, $NO_2$, $S(O)_m'R_{11}$, $SR_8$, $S(O)_mNR_8R_9$; $NR_8R_9$, $O(CR_{10}R_{20})_nNR_8R_9$, $C(O)R_8$, $CO_2R_8$, $CO_2(CR_{10}R_{20})_n'CONR_8R_9$, CN; $C(Z)NR_8R_9$, $NR_{10}S(O)_m R_{11}$, $NR_{10}C(Z)R_8$, $NR_{10}C(Z)NR_8R_9$, $C(Z)NR_8OR_9$, $N(OR_{21})C(Z)NR_8R_9$, $NR_{10}C(=NR_{15})NR_8R_9$, —$C(=NOR_{13})NR_8R_9$, 5-$(R_{18})$-1,2,4-oxadizaol-3-yl or 4-$(R_{12})$-5-$(R_{18}R_{19})$-4,5-dihydro-1,2,4-oxadiazol-3-yl.

A preferred monosubstituent for $Y_1$ when the aryl or heteroaryl group Q is mono-substituted include $(CR_{10}R_{20})_nY_2$ wherein: n is preferably 0, 1, 2 or 3, more preferably 0 or 1; and $Y_2$ is $OR_8$, especially where $R_8$ is hydrogen or $C_{1-10}$ alkyl; $NO_2$; $S(O)_mR_{11}$, especially where $R_{11}$ is $C_{1-10}$ alkyl; $SR_8$, especially where $R_8$ is $C_{1-10}$ alkyl; $S(O)_mNR_8R_9$, especially where $R_8$ and $R_9$ is each hydrogen or $C_{1-10}$ alkyl or $R_8$ and $R_9$ together with the nitrogen to which they are attached form a 5 to 7 membered ring which optionally includes another heteroatom selected from oxygen, sulfur or $NR_{12}$ and m is 2; n' is 1 to 10; —$NR_8R_9$, especially where $R_8$ and $R_9$ is each hydrogen, methyl or benzyl or $R_8$ and $R_9$ together with the nitrogen to which they are attached form a 5 to 7 membered ring which optionally includes another heteroatom selected from oxygen, sulfur or $NR_{12}$; $O(CR_{10}R_{20})_nNR_8R_9$, especially where $R_8$ and $R_9$ are each $C_{1-10}$ alkyl; $C(O)R_8$ especially where $R_8$ is hydrogen or $C_{1-10}$ alkyl; $CO_2R_8$, especially where $R_8$ is hydrogen or $C_{1-10}$ alkyl; $CO_2(CR_{10}R_{20})_n'CONR_8R_9$, especially where $R_8$ and $R_9$ is hydrogen or $C_{1-10}$ alkyl; CN; $C(Z)NR_8R_9$, especially where $R_8$ and $R_9$ is hydrogen or $C_{1-10}$ alkyl; $NR_{10}S(O)_mR_{11}$, especially where $R_{10}$ is hydrogen or $C_{1-10}$ alkyl and $R_{11}$ is $C_{1-10}$ alkyl or a halosubstituted; $NR_{10}C(Z)R_8$, especially where $R_8$ is $C_{1-10}$ alkyl and $R_{10}$ is hydrogen and Z is oxygen; $C(Z)NR_8OR_9$, especially where $R_8$ and $R_9$ is each hydrogen and Z is oxygen; $NR_{10}C(Z)NR_8R_9$, especially where $R_8$ and $R_9$ is each hydrogen or $C_{1-10}$ alkyl and Z is oxygen; $N(OR_{21})C(Z)NR_8R_9$, especially where $R_8$ especially where $R_8$, $R_9$ and $R_{21}$ is each hydrogen or $C_{1-10}$ alkyl and Z is oxygen; —$C(=NOR_{13})NR_8R_9$, especially where $R_8$, $R_9$ and $R_{13}$ is each hydrogen; $NR_{10}C(=NR_{15})NR_8R_9$, especially where $R_8$ and $R_9$ is hydrogen, $C_{1-10}$ alkyl or arylalkyl and $R_{15}$ is cyano; and 5-$(R_{18})$-1,2,4-oxadizaol-3-yl and 4-$(R_{12})$-5-$(R_{18}R_{19})$-4,5-dihydro-1,2,4-oxadiazol-3-yl, especially where $R_{12}$ is hydrogen and $R_{18}$ and $R_{19}$ is each hydrogen or $C_{1-10}$ alkyl or together are oxo.

When Q is disubstituted prefered substituents include those hereinbefore noted for use when Q is mono-substituted and, as further substituent(s), halogen and $C_{1-10}$ alkyl. When $R_3$ is phenyl substituted with two or three substituents, the alkyl moieties preferably have from one to three carbons, more preferably one. Preferred phenyl ring positions for two substituents are the 3- and 4-positions and, for three substituents, the 3-, 4- and 5- positions. The substituent at the 3- and 5-positions is preferably $C_{1-12}$ alkyl, such as methyl, or halogen, such as bromo, fluoro or chloro, while the substituent at the 4-position is preferably hydroxyl.

More preferably $Y_1$ is $(CR_{10}R_{20})_nY_2$, and n is 0 or 1; $Y_2$ is OH, or $S(O)_m'R_{11}$, especially where $R_{11}$ is $C_{1-10}$ alkyl; $SR_8$, especially where $R_8$ is $C_{1-10}$ alkyl; $NR_8R_9$, especially where $R_8$ and $R_9$ is hydrogen, alkyl, aryl alkyl, or aryl or $R_8$ and $R_9$ together with the nitrogen to which they are attached form a pyrrolidinyl, piperidinyl or morpholinyl ring, more prefereably the $R_8$ and $R_9$ terms in the $NR_8R_9$ moiety are hydrogen, methyl or benzyl; $CO_2R_8$, especially where $R_8$ is hydrogen or $C_{1-10}$ alkyl; $S(O)_m'NR_8R_9$, especially where $R_8$ and $R_9$ is each hydrogen or $C_{1-10}$ alkyl; $NR_{10}S(O)_mR_{11}$, especially where $R_{10}$ is hydrogen and $R_{11}$ is $C_{1-10}$ alkyl or 5-$(R_{18})$-1,2,4-oxadizaol-3-yl and 4-$(R_{12})$-5-$(R_{18}R_{19})$-4,5-dihydro-1,2,4-oxadiazol-3-yl, especially where $R_{12}$ is hydrogen and $R_{18}$ and $R_{19}$ is hydrogen or $C_{1-10}$ alkyl or together are oxo.

Most preferably, $Y_1$ is methylthio, ethylthio, methylsulfinyl, ethylsulfinyl, methylsulfonyl, N,N-dimethylaminomethyl, N-benzyl-N-methylaminomethyl, N-morpholinomethyl, methanesulfonamido, sulphonamidomethyl, 5-methyl-4,5-dihydro-1,2,4-oxadiazol-3-yl or 5,5-dimethyl-4,5-dihydro-1,2,4-oxadiazol-3-yl.

In all instances herein where there is an alkenyl or alkynyl moiety as a substituent group, such as in $R_5$, $R_8$, $R_9$, or $R_{11}$ the unsaturated linkage, i.e., the vinylene or acetylene linkage is preferably not directly attached to the nitrogen, oxygen or sulfur moieties, for instance in $Y_2$ as $C(Z)NR_8OR_9$, $NR_{10}C(Z)NR_8R_9$, or OR8.

As used herein, "optionally substituted" unless specifically defined shall mean such groups as halogen, such as fluorine, chlorine, bromine or iodine; hydroxy; hydroxy substituted $C_{1-10}$ alkyl; $C_{1-10}$ alkoxy, such as methoxy or ethoxy; halosubstituted $C_{1-10}$ alkoxy; S(O)m alkyl, wherein m is 0, 1 or 2, such as methyl thio, methylsulfinyl or methyl sulfonyl; amino, mono & di-substituted amino, such as in the $NR_7R_{17}$ group; or where the $R_7R_{17}$ may together with the nitrogen to which they are attached cyclize to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; halosubstituted $C_{1-10}$ alkyl, such $CF_3$; an optionally substituted aryl, such as phenyl, or an optionally substituted arylalkyl, such as benzyl or phenethyl, wherein these aryl moieties may also be substituted one to two times by halogen, hydroxy, hydroxy substituted alkyl, $C_{1-10}$ alkoxy, $S(O)_m$ alkyl, amino, mono & di-substituted amino, such as in the $NR_7R_{17}$ group, $C_{1-10}$ alkyl, or $CF_3$.

Preferred substitutions for $R_4$ when it is a 4-phenyl, 4-naphth-1-yl or 5-naphth-2-yl moiety are one or two substituents each independently selected from halogen, $SR_5$, $SOR_5$, $OR_{36}$, or $(CR_{10}R_{20})_mNR_{10}R_{20}$, and for other positions of substitution on these rings preferred substitution is halogen, $S(O)_mR_8$, $OR_8(CR_{10}R_{20})_mNR_{16}R_{26}$, $NR_{10}C(Z)R_8$ and $NR_{10}S(O)_mR_{11}$. More preferred substituents for the 4-position in phenyl and naphth-1-yl and on the 5-position in naphth-2-yl include halogen, especially fluoro and chloro, and $SR_5$ and $SOR_5$ wherein $R_5$ is preferably a $C_{1-2}$ alkyl, more preferably methyl; of which fluoro is especially preferred. Preferred substituents for the 3-position in phenyl and naphth-1-yl include: halogen, especially chloro; $OR_8$, especially $C_{1-4}$ alkoxy; amino; $NR_{10}C(Z)R_8$, especially $NHCO(C_{1-10}$ alkyl); and $NR_{10}S(O)_mR_{11}$, especially $NHSO_2(C_{1-10}$ alkyl). Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido.

A preferred grouping of Formula (I) are those compounds wherein $R_1$ is a 4-pyrimidiny ring, which ring is substituted by Y, and $R_2$ is hydrogen, an optionally substituted $C_{1-10}$ alkyl, optionally substituted $C_{3-7}$cycloalkyl, or an optionally substituted $C_{3-7}$cycloalkyl $C_{1-10}$ alkyl, an optionally substituted aryl, an optionally substituted heterocyclic alkyl, an optionally substituted heterocyclic, optionally substituted heteroaryl or heteroarylalkyl, $(CR_{10}R_{28})_n'OR_{13}$, $(CR_{10}R_{28})_n'S(O)_mR_{25}$, $(CR_{10}R_{28})_n'NR_8R_9$, $(CR_{10}R_{28})_n'C(Z)OR_{13}$, $(CR_{10}R_{28})_n'NHS(O)_2R_{25}$, $(CR_{10}R_{28})_n'C(Z)R_{13}$, or $(CR_{10}R_{28})_n'C(=NOR_{21})R_{13}$; and $R_1$, $R_3$, and $R_4$ are as defined for Formula (I).

More preferred are those compounds wherein $R_2$ is a $C_{1-4}$ alkyl (branched and unbranched), such as isopropyl, butyl, t-butyl, n-propyl, a methylthio propyl, a methylsulfinyl propyl, an amino propyl, N-methyl-N-benzylamino propyl group, (phenylmethyl)amino-1-propyl, diethylamino propyl, cyclopropyl methyl, morpholinyl butyl, morpholinyl propyl, morpholinyl ethyl, 1-Formyl-4-piperidinyl, 1-benzyl-4-piperidinyl, 1-methyl-4-piperidinyl, 1-ethoxycarbonyl-4-piperidinyl, phenyl substituted by halogen, thioalkyl or sulfinyl alkyl such as a methylthio, methylsulfinyl or methylsulfonyl moiety; and $R_1$, $R_3$, and $R_4$ are as defined for Formula (I).

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quarternary ammonium cations.

The following terms, as used herein, refer to:

"halo"—all halogens, that is chloro, fluoro, bromo and iodo;

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 5 to 8 carbons, which have at least one bond including but not limited to cyclopentenyl, cyclohexenyl, and the like.

"aryl"—phenyl and naphthyl;

"heteroaryl" (on its own or in any combination, such as "heteroaryloxy")—a 5–10 membered aromatic ring system in which one or more rings contain one or more heteroatoms selected from the group consisting of N, O or S, such as, but not limited, to pyrrole, quinoline, isoquinoline, pyridine, pyrimidine, oxazole, thiazole, thiadiazole, triazole, imidazole, or benzimidazole;

"heterocyclic" (on its own or in any combination, such as "heterocyclylalkyl")—a saturated or wholly or partially unsaturated 4–10 membered ring system in which one or more rings contain one or more heteroatoms selected from the group consisting of N, O, or S; such as, but not limited to, pyrrolidine, piperidine, piperazine, morpholine, imidazolidine or pyrazolidine;

"aroyl"—a C(O)Ar, wherein Ar is as phenyl, naphthyl, or aryl alkyl derivative such as defined above, such group include but are note limited to benzyl and phenethyl;

"alkanoyl"—a C(O)$C_{1-10}$ alkyl wherein the alkyl is as defined above;

"sulfinyl"—the oxide S(O) of the corresponding sulfide, while the term "thio" refers to the sulfide;

"aralkyl" or "heteroarylalkyl" or "heterocyclicalkyl" is used herein to mean an aryl, heteroaryl or heterocyclic moiety as respectively defined above said group connected to $C_{1-6}$ alkyl group as also defined above unless otherwise indicated.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

For the purposes herein of nomenclature, the compounds of formula (I) are named by their position corresponding to:

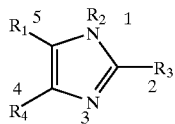

Exemplified compounds of formula (I) include:
2-(4-Methylthiophenyl)-4-(4-fluorophenyl)-5-(2-methoxy-4-pyrimidinyl)lmidazole;
2-(4-Methylsulfinylphenyl)-4-(4-fluorophenyl)-5-(2-methoxy-4-pyrimidinyl)imidazole;
2-[(4-N,N-Dimethyl)aminomethylphenyl]-4-(4-fluorophenyl)-5-(2-methoxy-4-pyrimidinyl)imidazole;
2-[(4-N,N-Dimethyl)aminomethylphenyl]-4-(4-fluorophenyl)-5-(2-phenoxy-4-pyridminyl)imidazole;
(+/−) 2-(4-Methylsulfinylphenyl)-4-(4-fluorophenyl)-5-(2-phenoxy-4-pyridminyl)imidazole;
2-(4-Methylthiophenyl]-4-(4-fluorophenyl)-5-(2-phenoxy-4-pyridminyl)imidazole;
and pharmaceutically acceptable salts thereof.

Compounds of formula (I) are imidazole derivatives which may be readily prepared using procedures well-known to those skilled in the art, and described in, for instance, Comprehensive Heterocyclic Chemistry, ed Katritzky and Rees, Pergamon Press, 1984, 5, 457–497, from starting materials which are either commercially available or can be prepared from such by analogy with well-known processes. A key step in many such syntheses is the formation of the central imidazole nucleus, to give compounds of formula (I). Suitable procedures are described in inter alia U.S. Pat. Nos. 3,707,475 and 3,940,486 which are herein incorporated by reference in their entirety. These patents describe the synthesis of a-diketones and a-hydroxyketones (benzoins) and their subsequent use in preparing imidazoles and N-hydroxyl imidazoles. Thereafter, further compounds of formula (I) may be obtained by manipulating substituents in any of the groups $R_1$, $R_2$, $R_3$ and $R_4$ using conventional functional group interconversion procedures.

Alternative synthesis for making compounds of Formula (I) are described in U.S. Ser. No. 08/481,671, Adams et al.; and in PCT/US93/00674, now U.S. Pat. No. 5,686,455, Adams et al., whose disclosures are incorporated by reference herein in their entirety.

Scheme I

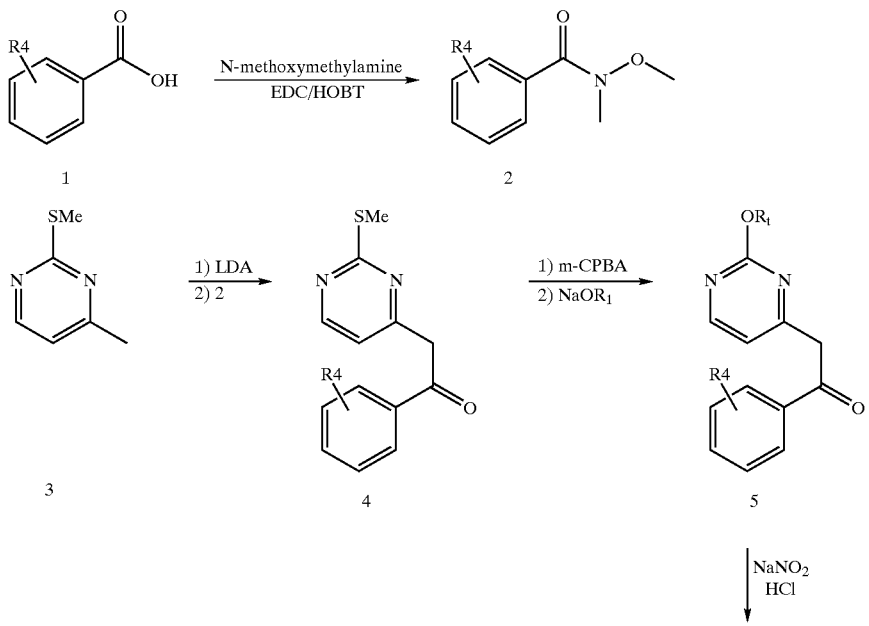

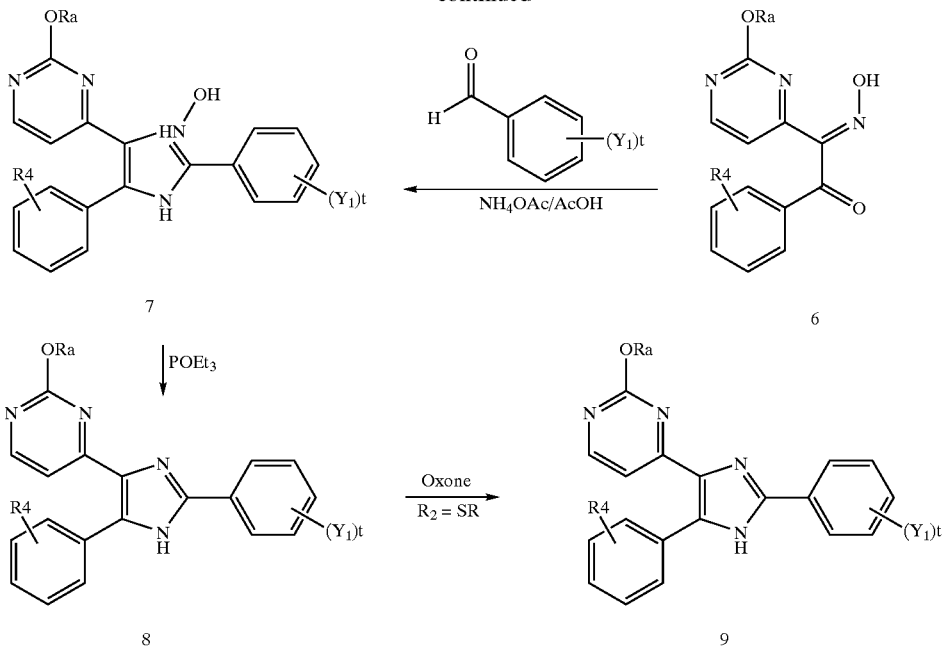

A benzoic acid is treated with N-methoxymethylamine, EDC and 1-hydroxy-benzotriazole to give N-methoxy,N-methyl-4-fluorobenzamide 4. Deprotonation of 4-methyl-2-thiomethylpyrimidine with a strong base such as lithium diisopropylamide followed by treatment with 4 yields an intermediate ketone, which upon treatment with an oxidant such as m-CPBA in an organic solvent such as methylene chloride followed by addition of an alkoxide or phenoxide yields alkoxy- or phenoxy-pyrimidine 5. This ketone may be treated with sodium nitrite and aqueous HCl to give keto-oxime 6. The keto-oxime is condensed with a substituted aromatic aldehyde and ammonium acetate in acetic acid to give imidazole-N-oxide 7. Treatment of the N-oxide with triethyl phosphite in an organic solvent such as N,N-dimethylacetamide or dimethylformamide at 100° C. yields 8. In cases where $R_2$ contains a thioether, treatment with an oxidant such as Oxone in an organic solvent such as methylene chloride yields the sulfoxide and sulfone 9.

A primary amine $R_3NH_2$ is treated (in Scheme II below) with 4-bromomethyl-2-methylthio-pyrimidine, 10 (prepared according to the procedure by Lucjan, S. et al, *J. Org. Chem.* 56, 5610, 1991), to give 11 which is then converted to the amide 12 by standard techniques. Deprotonation of 12 with a strong amide base, such as lithium di-iso-propyl amide or sodium bis-(trimethylsilyl)amide, followed by addition of an aryl nitrile to give the imidazole 13. Oxidation and displacement of the methylthio group as described above for compound 4 affords the alkoxypyrimidine 14.

Scheme II

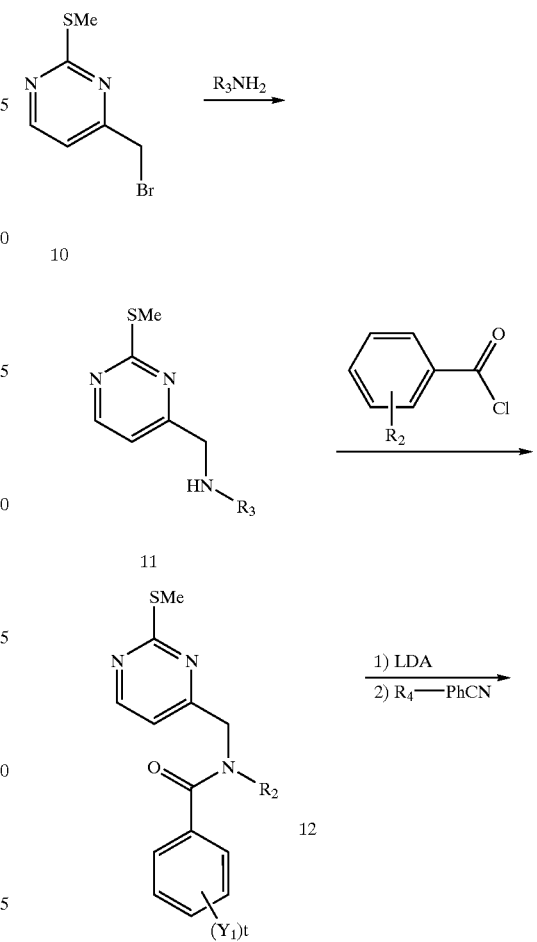

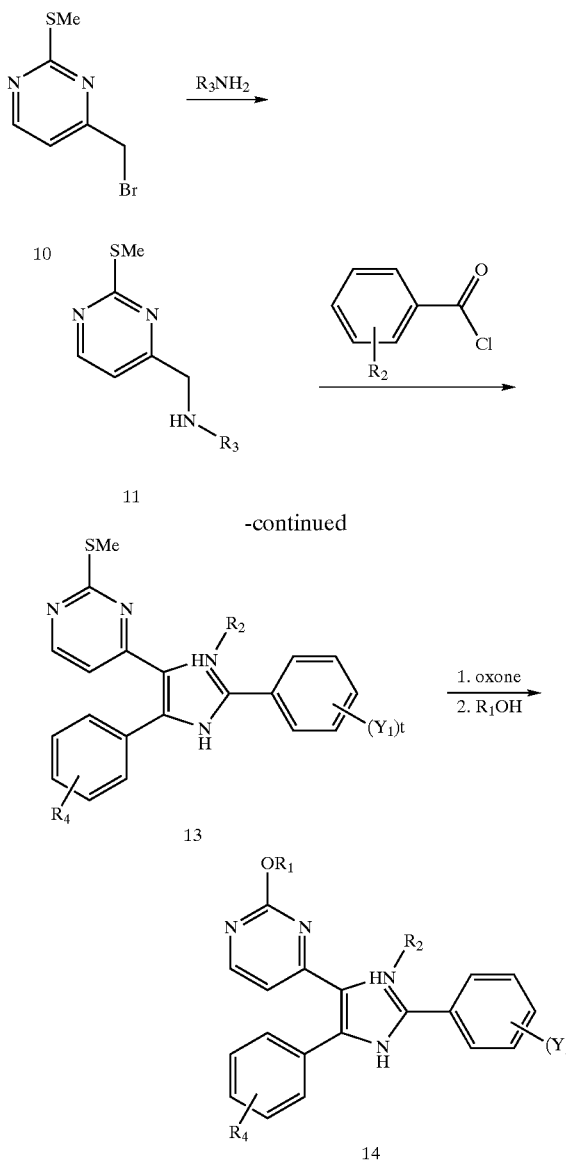

Once the imidazole nucleus has been established, further compounds of formula (I) which may be prepared by applying standard techniques for functional group interconversion, for instance: C(O)NR$_8$R$_9$ from CO$_2$CH$_3$ by heating with or without catalytic metal cyanide, e.g. NaCN, and HNR$_8$R$_9$ in CH$_3$OH; OC(O)R$_8$ from OH with e.g.,ClC(O)R$_8$ in pyridine; NR$_{10}$-C(S)NR$_8$R$_9$, from NHR$_{10}$ with an alkylisothiocyante or thiocyanic acid; NR$_6$C(O)OR$_6$ from NHR$_6$ with the alkyl chloroformate; NR$_{10}$(O)NR$_8$R$_9$, from NHR$_{10}$ by treatment with an isocyanate, e.g. HN=C=O or R$_{10}$N=C=O; NR$_{10}$—C(O)R$_8$ from NHR$_{10}$ by treatment with Cl—C(O)R$_8$ in pyridine; C(=NR$_{10}$)NR$_8$R$_9$ from C(NR$_8$R$_9$)SR$_8$ with H$_3$NR$_8$$^+$OAc$^-$ by heating in alcohol; C(NR$_8$R$_9$)SR$_8$ from C(S)NR$_8$R$_9$ with R$_6$-I in an inert solvent, e.g. acetone; C(S)NR$_8$R$_9$ (where R$_8$ or R$_9$ is not hydrogen) from C(S)NH$_2$ with HNR$_8$R$_9$, C(=NCN)—NR$_8$R$_9$, from C(=NR$_8$R$_9$)—SR$_8$ with NH$_2$CN by heating in anhydrous alcohol, alternatively from C(=NH)—NR$_8$NR$_9$ by treatment with BrCN and NaOEt in EtOH; NR$_{10}$—C(=NCN)SR$_8$ from NHR$_{10}$ by treatment with (R$_8$S)$_2$C=NCN; NR$_{10}$SO$_2$R$_8$ from NHR$_{10}$ by treatment with ClS$_2$R$_8$ by heating in pyridine; NR$_{10}$C(S)R$_8$ from NR$_{10}$C(O)R$_8$ by treatment with Lawesson's reagent [2,4-bis(4-methoxyphenyl)-1,3,2,4-dithiadiphosphetane-2,4-disulfide]; NR$_{10}$SO$_2$CF$_3$ from NHR$_6$ with triflic anhydride and base; NR$_{10}$(O)—C(O)—OR$_8$ from NHR$_{10}$ with, e.g. methyloxalyl chloride and a base such as triethylamine; NR$_{10}$C(O)—C(O)—NR$_8$R$_9$ from NR$_{10}$C(O)—C(O)—OR$_9$ with HNR$_8$R$_9$; and 1(NR$_{10}$)-2-imidazolyl from C(=NH)NHR$_{10}$ by heating with 2-chloroacetaldehyde in chloroform (wherein R$_8$, R$_9$ and R$_{10}$ are as hereinbefore defined.

Suitably, R$_6$ is C$_{1-4}$ alkyl, halo-substituted-C$_{1-4}$ alkyl, C$_{2-4}$ alkenyl, C$_{2-4}$ alkynyl or C$_{3-5}$ cycloalkyl.

Compounds of Formula (I) in which R$_2$ is hydrogen may be readily converted into further compounds of formula (I) in which R$_2$ is other than hydrogen for instance alkyl, by conventional procedures such as alkylation or acylation followed by reduction. Such methods are in general relatively inefficient as they lack regiospecificty and the desired N-1 product has to be separated from the mixture of N-1 and N-3 products. for instance by chromatography or fractional crystallisation.

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, (CR$_{10}$R$_{20}$)$_n$. Suitable examples of imidazole nitrogen protecting groups include tetrahydropyranyl.

It should be noted that the compounds of Formula (I), where R$_4$ may be an alkylsulfinyl, arylsulfinyl, alkylsulfonyl, or arylsulfonyl are prodrugs which are reductively converted in vivo to the corresponding alkylthio or arylthio form.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

2-(4-Methylthiophenyl)-4-(4-fluorophenyl)-5-(2-methoxy-4-pyrimidinyl)imidazole a) N-Methyl,N-methoxy-4-fluorobenzamide To a mixture of 4-fluorobenzoic acid (5.0 grams (hereinafter "g"), 36 millimoles (hereinafter "mmol")) and N,O-dimethylhydroxylamine hydrochloride (3.8 g, 39 mmol) in 200 mL of CH$_2$Cl$_2$ at 0° C. was added triethylamine (5.0 milliliters (hereinafter "mL"), 36 mmol). The solution was warmed to room temperature and 4-dimethylaminopyridine (0.2 g, 1.6 mmol) and 1-(dimethylaminopropyl)-3-ethylcarbodiimide (6.8 g, 36 mmol) were added. The resulting solution was stirred for 16 hours (hereinafter "h"). Next, the solution was diluted with 200 mL of ethyl acetate and washed with 100 mL of saturated NaHCO$_3$, 50 mL of H$_2$O, twice with 50 mL of 1N HCl, and 50 mL of H$_2$O. The organic layer was dried over MgSO$_4$, filtered and concentrated under reduced pressure to give a light yellow oil. The oil was purified by chromatography through a plug of silica gel with 50% ethyl acetate/ hexane to give title compound as a light yellow oil (5.5 g, 85%). ES(+)MS m/e=184 (MH$^+$)

b) 4-(2-Methylthiopyrimidinyl)methyl-4-fluorophenylketone

To a solution of lithium diisopropylamide (29.5 mmol) in 40 mL ethylene glycol dimethyl ether at −20° C. was added a cooled solution of 2-methylthio-4-methylpyrimidine (3.17 g, 22.7 mmol) in 10 mL of ethylene glycol dimethyl ether via cannula. The resulting solution was stirred for 30 min and then treated with a cooled solution of N-methyl,N-methoxy-4-fluorobenzamide (4.56 g, 24.9 mmol) in 10 mL of ethylene glycol dimethyl ether via cannula. This solution was warmed to room temperature and then heated at 40° C. for 1 h. Next, the solution was cooled to room temperature and 300 mL of H$_2$O were added. The mixture was extracted thrice with 150 mL of ethyl acetate. The combined organic layers were dried over MgSO$_4$, filtered and concentrated under reduced pressure to give an orange solid. The solid was purified by chromatography through a plug of silica gel with 20–40% ethyl acetate/hexane to give 5 g of a dark yellow solid. This solid was recrystallized from ethyl ether/hexane to give the title compound as yellow needles (4.2 g, 70%). ES(+)MS m/e=263 (MH$^+$)

c) 4-(2-Methoxypyrimidinyl)methyl-4-fluorophenylketone

To a solution of 4-(2-methylthiopyrimidinyl)methyl-4-fluorophenylketone (1.5 g, 5.7 mmol) in 75 mL of CH$_2$Cl$_2$ at 0° C. was added 85% 4-chloroperoxybenzoic acid (1.39 g, 6.8 mmol) and the resulting solution was stirred for 2 h. The solution was washed with 30 mL of 20% Na$_2$S$_2$O$_5$, 30 ML of sat. NaHCO$_3$, and 30 mL brine. The organic layer was dried over MgSO$_4$, filtered and concentrated under reduced pressure to give 4-(2-methylsulfinylpyrimidinyl)methyl-4-fluorophenylketone as a yellow solid.

To a solution of 4-(2-methylsulfinylpyrimidinyl)methyl-4-fluorophenylketone (5.7 mmol) in 75 mL THF was added 22 mL of 25% NaOMe in MeOH at 0° C. The solution was warmed to room temperature and stirred for 1 h. The solution was then heated at 50° C. for 30 min. Next, the solution was cooled, 200 mL of H$_2$O were added and it was extracted thrice with 100 mL of ethyl acetate. The combined organic layers were dried over MgSO$_4$, filtered and concentrated under reduced pressure to give a solid. The solid was then purified by silica gel chromatography with 15–30% ethyl acetate/hexane to give the title compound as a light yellow solid (0.8 g, 57%). ES(+)MS m/e=247 (MH$^+$)

d) 1-(2-Methoxy-4-pyrimidyl)-2-(4-fluorophenyl)-ethanedione-1-oxime

To a suspension of 4-(2-methoxypyrimidinyl)methyl-4-fluorophenylketone (0.70 g, 2.9 mmol) in 32 mL of 1:1 3N HCl:dioxane was added a solution of sodium nitrite (0.24 g, 3.4 mmol) in 8 mL of H$_2$O. The mixture was stirred for 3.5 h and then made basic by addition of NH$_4$H (conc.). The mixture was extracted thrice with 50 mL ethyl ether. The combined organic layers were dried over MgSO$_4$, filtered and concentrated under reduced pressure to give the title compound as a light green solid (0.87 g, quantitative). ES(+)MS m/e=276 (MH$^+$)

e) 2-(4-Methylthiophenyl)-4-(4-fluorophenyl)-5-(2-methoxy-4-pyrimidinyl)imidazole-N-oxide To 1-(2-methoxy-4-pyrimidinyl)-2-(4-fluorophenyl)-ethanedione, 1-oxime (0.44 g, 1.4 mmol) in 16 mL of acetic acid was added 4-methylthiobenzaldehyde (0.29 mL, 2.1 mmol) and NH$_4$OAc (0.88 g, 11.4 mmol). The resulting solution was heated to reflux for 24 h, cooled and poured into 100 mL of H$_2$O. The solution was made basic with by addition of NH$_4$OH (conc.) and extracted thrice with 50 mL of CH$_2$Cl$_2$. The combined organic layers were dried over MgSO$_4$, filtered and concentrated under reduced pressure to give an orange oil. The oil was purified by silica gel chromatography with 30–60% ethyl acetate/hexane to give the title compound as a yellow-orange solid (0.18 g, 28%). ES(+)MS m/e=409 (MH$^+$)

f) 2-(4-Methylthiophenyl)-4-(4-fluorophenyl)-5-(2-methoxy-4-pyrimidinyl)imidazole To a solution of 2-(4-methylthiophenyl)-4-(4-fluorophenyl)-5-(2-methoxy-4-pyrimidinyl)imidazole (0.16 g, 0.38) in 4 mL of N,N-dimethylacetamide was added triethyl phosphite (0.10 mL, 0.57 mmol) and the solution was heated overnight at 100° C. More triethyl phosphite (0.066 mL, 0.38 mmol) was added and the solution was heated at 100° C. for an additional 4 h. The solution was concentrated to a small volume under reduced pressure and H$_2$O was added. The mixture was extracted thrice with 20 mL CH$_2$Cl$_2$. The combined organic layers were dried over MgSO$_4$, filtered and concentrated under reduced pressure to give a yellow oil. The oil was purified by silica gel chromatography with 20–50% ethyl acetate/hexane to give an orange oil which precipitated upon addition of a small amount of acetonitrile. The precipitate was triturated with hexane to remove residual amount of triethyl phosphite to give a yellow solid (0.11 g, 99%). ES(+)MS m/e=393 (MH$^+$)

Example 2

2-(4-Methylsulfinylphenyl)-4-(4-fluorophenyl)-5-(2-methoxy-4-pyrimidinyl)imidazole To a solution of 2-(4-methylthiophenyl)-4-(4-fluorophenyl)-5-(2-methoxy-4-pyrimidinyl)imidazole (0.10 g, 0.25 mmol) in 10 mL of THF at 0° C. was added a cooled solution of Oxone (0.084 g, 0.28 mmol) in 10 mL of H$_2$O. The solution was warmed to room temperature and stirred for 20 min. Next, 20 mL of NaHCO$_3$ sat was added and the mixture was extracted thrice with 20 mL of CH$_2$Cl$_2$. The combined organic layers were washed with 20 mL of 20% NaS$_2$O$_5$ and brine and then dried over MgSO$_4$, filtered and concentrated under reduced pressure. The resulting residue was then purified by silica gel chromatography with 2–6% CH$_3$OH/CH$_2$Cl$_2$ to give the title compound as a light yellow solid (0.084 g, 82%). ES(+) MS m/e=409 (MH$^+$)

Example 3

2-[(4-N,N-Dimethyl)aminomethylphenyl]-4-(4-fluorophenyl)-5-(2-methoxy-4-pyrimidinyl) imidazole a) 4-N,N-Dimethylaminomethylbenzaldehyde diethylacetal To a solution of dimethylamine hydrochloride (16.6 g 204 mmol) in 120 mL of methanol was added potassium hydroxide (3.6 g, 64 mmol). The mixture was stirred for 10 min at room temperature and 4-(diethoxymethyl)benzaldehyde (29.4 g, 141 mmol) was added. The mixture was cooled to 0° C., and sodium cyanoborohydride was added. The reaction was stirred at rt for 2.5 h. The mixture was made basic with 10% sodium hydroxide at 0° C. The mixture was filtered, and the filtrate was evaporated under reduced pressure. The residue was acidified with 3 N hydrochloric acid at 0° C. and washed with ether. The aqueous layer was made basic with 10% sodium hydroxide, extracted with methylene chloride (2×), the combined organic extracts were dried (MgSO4), evaporated under reduced pressure and the residue purified by silica gel chromatography to yield 19 g of the title compound. $^1$H NMR (CDCl$_3$) d 1.22 (t, J=6.3 Hz, 6H), 2.23 (s, 6H), 3.40 (s, 2H), 3.5–3.7 (m, 4H), 5.49 (s, 1H), 7.29 (d, J=9 Hz, 2H), 7.41 (d, J=9 Hz, 2H).

b) 2-[(4-N,N-Dimethyl)aminomethylphenyl]-4-(4-fluorophenyl)-5-(2-methoxy-4-pyrimidinyl)imidazole-N-oxide To 1-(2-methoxy-4-pyrimidinyl)-2-(4-fluorophenyl)-ethanedione, 1-oxime (0.43 g, 1.4 mmol) in 16 mL of acetic acid was added 4-N,N-dimethylaminomethylbenzaldehyde diethylacetal (0.50 g, 2.1 mmol) and $NH_4OAc$ (0.88 g, 11.4 mmol). The resulting solution was heated 120° C. for 20 hours, cooled and poured into 150 mL of $H_2O$. The solution was made basic with by addition of $NH_4OH$ (conc.) and extracted thrice with 50 mL of $CH_2Cl_2$. The combined organic layers were dried over $MgSO_4$, filtered and concentrated under reduced pressure. The residue was then purified by chromatography through a plug of silica gel with 10–30% $CH_3OH/CH_2Cl_2$ to give the title compound as a yellow foam (0.30 g, 50%). ES(+)MS m/e=420 (MH$^+$)

c) 2-[4-(N,N-Dimethylaminomethyl)phenyl]-4-(4-fluorophenyl)-5-(2-methoxy-4-pyrimidinyl)imidazole To a solution of 2-[4-(N,N-Dimethylaminomethyl)phenyl]-4-(4-fluorophenyl)-5-(2-methoxy-4-pyrimidinyl)imidazole-N-oxide (0.24 g, 0.58) in 7 mL of N,N-dimethylacetamide was added triethyl phosphite (0.30 mL, 1.74 mmol) and the solution was heated at 110° C. overnight. The solution was concentrated to a small volume under reduced pressure and $H_2O$ was added. The mixture was extracted thrice with 20 mL of $CH_2Cl_2$. The combined organic layers were dried over $MgSO_4$, filtered and concentrated under reduced pressure to give a yellow oil. The oil was dissolved in 20 mL of $H_2O$ with 3 mL of 3 N HCl and washed thrice with 10 mL of ethyl acetate. The aqueous solution was made basic with 1 mL of 50% NaOH and extracted thrice with 20 mL of $CH_2Cl_2$. The oil was triturated with hexane to remove any residual amount of $P(OEt)_3$. The oil was purified by reverse phase preparative HPLC to give the TFA salt of the title compound as a yellow solid (0.034 g, 7.6%). ES(+)MS m/e=404 (MH$^+$)

Example 4

2-(4-Methylthiophenyl)-4-(4-fluorophenyl)-5-(2-phenoxy-4-pyrimidinyl)imidazole a) 4-(2-Phenoxypyrimidinyl)methyl-4-fluorophenylketone To a solution of 4-(2-methylthiopyrimidinyl)methyl-4-fluorophenylketone (1.5 g, 5.7 mmol) in 75 mL of $CH_2Cl_2$ at 0° C. was added 85% 4-chloroperoxybenzoic acid (1.39 g, 6.8 mmol) and the resulting solution was stirred for 1 h at room temperature. The solution was washed with 30 mL of 20% $Na_2S_2O_5$, 30 mL of sat. $NaHCO_3$, and 30 mL of brine. The organic layer was dried over $MgSO_4$, filtered and concentrated under reduced pressure to give 4-(2-methylsulfinylpyrimidinyl)methyl-4-fluorophenylketone as a yellow solid.

To a solution of phenol (2.72 g, 29 mmol) in 100 mL of dry THF at 0° C. was added 60% sodium hydride in mineral oil (0.55 g, 13.8 mmol) and the mixture was warmed to room temperature. To the suspension of sodium phenoxide was added a solution of 4-(2-methylsulfinylpyriridinyl)methyl-4-fluorophenylketone (5.7 mmol) in 10 mL of THF. The mixture was heated at 50° C. for 16 h. The mixture was concentrated under reduced pressure and 10 mL of N,N-dimethylacetamide was added. The resulting solution was heated at 80° C. for 1 h. The solution was cooled, 200 mL of $H_2O$ were added and the resulting mixture was extracted thrice with 100 mL of ethyl acetate. The combined organic layers were dried over $MgSO_4$, filtered and concentrated under reduced pressure to give a solid. The solid was then purified by silica gel chromatography with 20–40% ethyl acetate/hexane to give the title compound as a light yellow solid (0.79 g, 44%). ES(+)MS m/e=309 (MH$^+$)

b) 1-(2-Phenoxy-4-pyrimidinyl)-2-(4-fluorophenyl)-ethanedione, 1-oxime

Following the procedure of Example 1d except using 4-(2-phenoxy-pyrimidinyl)methyl-4-fluorophenylketone afforded the title compound as a yellow foam in 91% yield. ES(+)MS m/e=338 (MH$^+$)

c) 2-(4-Methylthiophenyl)-4-(4-fluorophenyl)-5-(2-phenoxy-4-pyrimidinyl)imidazole-N-oxide Following the procedure of Example 1e except using 1-(2-phenoxy-4-pyrimidinyl)-2-(4-fluorophenyl)-ethanedione, 1-oxime afforded the title compound as a yellow solid in 85% yield. ES(+)MS m/e=471 (MH$^+$)

d) 2-(4-Methylthiophenyl)-4-(4-fluorophenyl)-5-(2-phenoxy-4-pyrimidinyl)imidazole Following the procedure of Example 1f except using 2-(4-methylthiophenyl)-4-(4-fluorophenyl)-5-(2-phenoxy-4-pyrimidinyl)imidazole-N-oxide afforded the title compound as a yellow foam in 75% yield. ES(+)MS m/e=455 (MH$^+$)

Example 5

2-(4-Methylsulfinylphenyl)-4-(4-fluorophenyl)-5-(2-phenoxy-4-pyrimidinyl)imidazole Following the procedure of Example 2 except using 2-(4-methylthiophenyl)-4-(4-fluorophenyl)-5-(2-phenoxy-4-pyrimidinyl)imidazole afforded the title compound as a white solid (after crystallizing from a small amount of $CH_2Cl_2$) in 60% yield. ES(+)MS m/e=471 (MH$^+$)

Example 6

2-[4-(N,N-Dimethylaminomethyl)phenyl]-4-(4-fluorophenyl)-5-(2-phenoxy-4-pyrimidinyl)imidazole a) 2-[4-(N,N-Dimethylaminomethyl)phenyl]-4-(4-fluorophenyl)-5-(2-phenoxy-4-pyrimidinyl)imidazole-N-oxide Following the procedure of Example 3b except using 1-(2-phenoxy-4-pyrimidinyl)-2-(4-fluorophenyl)-ethanedione, 1-oxime afforded the title compound as a yellow foam in 57% yield. ES(+)MS m/e=482 (MH$^+$)

b) 2-[4-(N,N-Dimethylaminomethyl)phenyl]-4-(4-fluorophenyl)-5-(2-phenoxy-4-pyrimidinyl)imidazole To a solution of 2-[4-(N,N-Dimethylaminomethyl)phenyl]-4-(4-fluorophenyl)-5-(2-phenoxy-4-pyrimidinyl)imidazole-N-oxide (0.32 g, 0.66 mmol) in 5 mL of N,N-dimethylacetamide was added triethyl phosphite (0.34 mL, 2.0 mmol) and the solution was heated at 95° C. overnight. The solution was concentrated to a small volume under reduced pressure and $H_2O$ was added. The mixture was extracted thrice with 20 mL of $CH_2C_2$. The combined organic layers were dried over $MgSO_4$, filtered and concentrated under reduced pressure to give a yellow oil. The oil was purified by silica gel chromatography using 5–15% $CH_3OH/CH_2Cl_2$ to give the title compound as a yellow foam (0.094 g, 30%). ES(+)MS m/e=466 (MH$^+$)

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX- 1 is not effected by compounds of Formula (1). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

Accordingly, the present invention provides a method of treating a cytokine-mediated disease which comprises administering an effective cytokine-interferring amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of formula (I) or a pharmaceutically acceptable salt thereof.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of formula (I) or a pharmaceutically acceptable salt thereof Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

Compounds of formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL-8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of IL-1, IL-8 or TNF mRNA above basal levels in cells or tissues in which IL-1, IL-8 or TNF, respectively, is produced.

The discovery that the compounds of formula (I) are inhibitors of cytokines, specifically IL-1, IL-8 and TNF is based upon the effects of the compounds of formulas (I) on the production of the IL-1, IL-8 and TNF in in vitro assays which are described herein.

As used herein, the term "inhibiting the production of IL-1 (IL-8 or TNF)" refers to:

a) a decrease of excessive in vivo levels of the cytokine (IL-1, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-8 or TNF) in a human to normal or sub-normal levels;

c) a down regulation, by inhibition of the direct synthesis of the cytokine (IL-1, IL-8 or TNF) as a postranslational event; or d) a down regulation, at the translational level, of excessive in vivo levels of the cytokine (IL-1, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphoctye cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-$\beta$).

As used herein, the term "cytokine interfering" or "cytokine suppresive amount" refers to an effective amount of a compound of formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-$\beta$ (also known as lymphotoxin) has close structural homology with TNF-a (also known as cachectin) and since each induces similar biologic responses and binds to the same cellular receptor, both TNF-a and TNF-$\beta$ are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories recently [See Lee et al., Nature, Vol. 300 n(72), 739–746 (1994)]. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lo lipopolysaccharide in cytokine production in macrophages. In addition to those diseases already noted herein, treatment of stroke, neurotrauma, cardiac and renal reperfusion injury, congestive heart failure, thrombosis, chronic renal failure, glomerulonephritis, angiogenesis & related processes, such as cancer, diabetes and pancreatic $\beta$ cells diseases, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). B *Ann. N. Y Acad. Sci.* 696, 149–170.

Another aspect of the present invention is to the novel use of these CSBP/cytokine inhibitors for the treatment of chronic inflammatory or proliferative or angiogenic diseases which are caused by excessive, or inappropriate angiogenesis.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non- systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to 30 mg/kg, more preferably from about 0.5 mg to 15mg. The daily parenteral dosage regimen about 0.1 to about 80 mg/kg of total body weight, preferably from about 0.2 to about 30 mg/kg, and more preferably from about 0.5 mg to 15mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

BIOLOGICAL EXAMPLES

The cytokine-inhibiting effects of compounds of the present invention were determined by the following in vitro assays:

Interleukin—1 (IL-1), Interleukin-8 (IL-8), and Tumour Necrosis Factor (TNF) assays may be found in a number of publications, in particular suitable assays for use herein are described in Adams et al., U.S. 5,593,992, whose disclosure is incorporated by reference.

In vivo TNF assay:

While the above indicated assay in an in vitro assay, the compounds of Formula (I) may also be tested in an in vivo system such as described in (1) Griswold et al., *Drugs Under Exp. and Clinical Res.,XIX* (6), 243–48 (1993); or (2) Boehm, et al., *Journal Of Medicinal Chemistry* 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at $-20°$ C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat anti-rabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production In Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37° C. Following a 4 hour incubation, the tubes were centrifuged at 5000 rpm for 5 minutes in a TOMY microfuge, plasma was withdrawn and frozen at $-80°$ C.

Cytokine measurement: IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP Kinase Assay:

This assay measures the CSBP-catalyzed transfer of $^{32}p$ from [a-$^{32}$P]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 mM Hepes buffer, pH 7.5; 10 mM $MgCl_2$; 170 uM ATP($^1$); 10 uM Na ortho vanadate; 0.4 mM T669 peptide; and 20–80 ng of yeast-expressed purified CSBP2 (see Lee et al., Nature 300, n(72), 739–746 (Dec. 1994)). Compounds (5 ul from [6×] stock(²)) are pre-incubated with the enzyme and peptide for 20 min on ice prior to starting the reactions with 32P/MgATP. Reactions are incubated at 30° C. for 10 min and stopped by adding 10 μl of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

(1) The Km of CSBP for ATP was determined to be 170 uM. Therefore, compounds screened at the Km value of ATP.

(2) Compounds are usually dissolved in DMSO and are diluted in 25 mM Hepes buffer to get final concentration of DMSO of 0.17%.

Representative compounds of Formula (1), Examples 1 to 6 have all demonstrated positive inhibitory activity of an $IC_{50}$ of <50 uM in this binding assay.

Prostoglandin endoperoxide synthase-2 (PGHS-2) assay:

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593,992 whose disclosure is incorporated herein by reference.

TNF-a in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF- a is able to induce nerve growth factor (NGF) and stimulate the release of other cytokines from activated astrocytes, this post-traumatic alteration in gene expression of TNF-a plays an important role in both the acute and regenerative response to CNS trauma. A suitable assay may be found in WO 97/35856 whose disclosure is incorporated herein by reference.

CNS Injury model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosrue is incorporated herein by reference, is an assay for determination of inflammatory angiogenesis which may be used to show that cytokine inhibition will stop the tissue destruction of excessive or inappropriate proliferation of blood vessels.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaborations it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I):

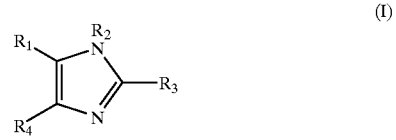

wherein:

$R_1$ is 4-pyrimidinyl ring which ring is substituted by Y, or $NHR_a$, and is optionally substituted independently one to three times with Y, $NHR_a'$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is $X_1$–$R_a$;

$X_1$ is sulfur or oxygen;

$R_a$ is aryl, aryl$C_{1-6}$ alkyl, heterocyclic, heterocyclyl$C_{1-6}$ alkyl, heteroaryl, or heteroaryl$C_{1-6}$alkyl, wherein each of these moieties may be optionally substituted;

$R_a'$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_2$ is hydrogen, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{28})_nOR_{12}$, $(CR_{10}R_{28})_n'OR_{13}$, $(CR_{10}R_{28})_nS(O)_mR_{25}$, $(CR_{10}R_{28})_n$ $S(O)_2R_{25}$, $(CR_{10}R_{28})_n'NHS(O)_2R_{25}$, $(CR_{10}R_{28})_n'NR_8R_9$, $(CR_{10}R_{28})_n'NO_2$, $(CR_{10}R_{28})_n'CN$, $(CR_{10}R_{28})_n'S(O)_mNR_8R_9$, $(CR_{10}R_{28})_n'C(Z)R_{13}$, $(CR_{10}R_{28})_n'C(Z)OR_{13}$, $(CR_{10}R_{28})_n'C(Z)NR_8R_9$, $(CR_{10}R_{28})_n'C(Z)NR_{13}OR_{12}$, $(CR_{10}R_{28})_n'NR_{10}C(Z)R_{13}$, $(CR_{10}R_{28})_n'NR_{10}C(Z)NR_8R_9$, $(CR_{10}R_{28})_nN(OR_{21})C(Z)NR_8R_9$, $(CR_{10}R_{28})_n'N(OR_{21})C(Z)R_{13}$, $(CR_{10}R_{28})_n'C(=NOR_{21})R_{13}$, $(CR_{10}R_{28})_n'NR_{10}C(=NR_{27})NR_8R_9$, $(CR_{10}R_{28})_n'OC(Z)NR_8R_9$, $(CR_{10}R_{28})_n'NR_{10}C(Z)OR_{10}$, $(CR_{10}R_{28})_n'NR_{10}C(Z)OR_{10}$, 5-($R_{25}$)-1,2,4-oxadizaol-3-yl or 4-($R_{12}$)-5-($R_{18}R_{19}$)-4,5-dihydro-1,2,4-oxadiazol-3-yl; wherein the cyclcoalkyl, cycloalkyl alkyl, aryl, arylalkyl, heteroaryl, heteroarylalkyl, heterocyclyl, or heterocyclylalkyl moieties may be optionally substituted;

n is 0 or an integer from 1 to 10;

n' is an integer having a value of 1 to 10;

m is 0, or the integer 1 or 2;

m' is an integer having a value of 1 or 2, m" is 0, or an integer having a value of 1 to 5;

t is a number having a value of 1, 2 or 3;

v is 0, or an integer having a value of 1 or 2;

$R_3$ is $Q-(Y_1)_t$;

Q is an aryl or heteroaryl group;

Z is oxygen or sulfur;

$Y_1$ is independently selected from hydrogen, $C_{1-5}$ alkyl, halo-substituted $C_{1-5}$ alkyl, halogen, or $(CR_{10}R_{20})_nY_2$;

$Y_2$ is $OR_8$, $NO_2$, $S(O)_m"R_{11}$, $SR_8$, $S(O)_m"OR_8$, $S(O)_m NR_8R_9$, $NR_8R_9$, $O(CR_{10}R_{20})_n'NR_8R_9$, $C(O)R_8$, $CO_2R_8$, $CO_2(CR_{10}R_{20})_n'CONR_8R_9$, $ZC(O)R_8$, $CN$, $C(Z)NR_8R_9$, $NR_{10}C(Z)R_8$, $C(Z)NR_8OR_9$, $NR_{10}C(Z)NR_8R_9$, $NR_{10}S(O)_m"R_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR13)ZR_{11}$, $OC(Z)NR_8R_9$, $NR_{10}S(O)_m"CF_3$, $NR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, nitro, cyano, $C(Z)NR_7R_{17}$, $C(Z)OR_{23}$, $(CR_{10}R_{20})_vCOR_{36}$, $SR_5$, $SOR_5$, $OR_{36}$, halo-substituted-$C_{1-4}$ alkyl, $C_{1-4}$ alkyl, $ZC(Z)R_{36}$, $NR_{10}C(Z)R_{23}$, or $(CR_{10}R_{20})_v NR_{10}R_{20}$ and which, for other positions of substitution, is halo, nitro, cyano, $C(Z)NR_{16}R_{26}$, $C(Z)OR_8$, $(CR_{10}R_{20})_m"COR_8$, $S(O)_m R_8$, $OR_8$, halo-substituted-$C_{1-4}$ alkyl, $C_{1-4}$ alkyl, $CR_{10}R_{20})_m"NR_{10}C(Z)R_8$, $NR_{10}S(O)_m'R_{11}$, $NR_{10}S(O)_m'$ $NR_7R_{17}$, $ZC(Z)R_8$ or $(CR_{10}R_{20})_m"NR_{16}R_{26}$;

$R_5$ is hydrogen, $C_{1-4}$ alkyl, $C_{2-4}$ alkenyl, $C_{2-4}$ alkynyl or $NR7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, $C(Z)R_{13}$ or optionally substituted $C_{1-4}$ alkyl, optionally substituted aryl, optionally substituted aryl$C_{1-4}$ alkyl, or $S(O)_2R_{25}$;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl, wherein all of these moieties may be optionally substituted;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{18}$ and $R_{19}$ is each independently selected from hydrogen, $C_{1-4}$ alkyl, substituted alkyl, optionally substituted aryl, optionally substituted arylalkyl or together denote a oxygen or sulfur;

$R_{21}$ is hydrogen, a pharmaceutically acceptable cation, $C_{10}$ alkyl, $C_{3-7}$ cycloalkyl, aryl, aryl $C_{1-4}$ alkyl, heteroaryl, heteroarylalkyl, heterocyclyl, aroyl, or $C_{1-10}$ alkanoyl;

$R_{22}$ is $R_{10}$ or $C(Z)$-$C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

$R_{25}$ is $C_{1-10}$ alkyl, $C_{3-7}$ cycloalkyl, heterocyclyl, aryl, arylalkyl, heterocyclyl, heterocyclyl-$C_{1-10}$-alkyl, heteroaryl or heteroarylalkyl;

$R_{27}$ is hydrogen, cyano, $C_{1-4}$ alkyl, $C_{3-7}$ cycloalkyl, or aryl;

$R_{28}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

or a pharmaceutically acceptable salt thereof.

2. The compound according to claim 1 wherein $R_1$ is a 4-pyrimidinyl group substituted by Y.

3. The compound according to claim 2 wherein $X_1$ is oxygen, and $R_a$ is an optionally substituted aryl or an optionally substituted arylalkyl.

4. The compound according to claim 2 wherein Ra' is optionally substituted $C_{1-4}$ alkyl.

5. The compound according to claim 1 wherein $R_2$ is hydrogen, optionally substituted $C_{1-4}$ alkyl group, an optionally substituted aryl, an optionally substituted heterocyclyl, or an optionally substituted heterocyclyl$C_{1-10}$ alkyl.

6. The compound according to claim 1 wherein Q is an optionally substitued phenyl.

7. The compound according to claim 6 wherein Q is phenyl substitued independently by halogen, halosubstituted alkyl, or $(CR_{10}R_{20})_nY_2$ and $Y_2$ is $OR_8$, $S(O)_m'R_{11}$, $SR_8$, $S(O)_mNR_8R_9$, or $NR_8R_9$.

8. The compound according to claim 1 wherein $R_4$ is optionally substituted phenyl, naphth-1-yl or naphth-2-yl wherein the 4-phenyl, 4-naphth-1-yl or 5-naphth-2-yl moiety are substituted by one or two substituents each independently selected from halogen, $SR_5$, $SOR_5$, $OR_{36}$, or $(CR_{10}R_{20})_mNR_{10}R_{20}$, and for other positions of substitution on these rings the substitution is halogen, $S(O)_mR_8$, $OR_9$, $(CR_{10}R_{20})_mNR_{16}R_{26}$, $NR_{10}C(Z)R_8$ and $NR_{10}S(O)_mR_{11}$.

9. The compound according to 8 wherein the substituent in the 4-position for phenyl and naphth-1-yl and on the 5-position in naphth-2-yl is fluoro, chloro, $SR_5$ or $SOR_5$.

10. The compound of formula (I), according to claim 1, which is:

2-[(4-N,N-Dimethyl)aminomethylphenyl]-4-(4-fluorophenyl)-5-(2-phenoxy4-pyrimidinyl)imidazole;

(+/−) 2-(4-Methylsulfinylphenyl]-4-(4-fluorophenyl)-5-(2-phenoxy-4-pyrimidinyl)imidazole;

2-(4-Methylthiophenyl]-4-(4-fluorophenyl)-5-(2-phenoxy-4-pyrimidinyl)imidazole; or a pharmaceutically acceptable salt thereof.

11. A pharmaceutical composition comprising an effective amount of a compound according to claim 1, and a pharmaceutically acceptable carrier or diluent.

12. A method of prophylaxis, or the treatment of a CSBP/RK/p38 kinase mediated disease in a mammal in need thereof, which method comprises administering to said mammal an effective amount of a compound of Formula (I) according to claim 1.

13. The method according to claim 12 wherein the disease is psoriatic arthritis, Reiter's syndrome, rheumatoid arthritis, gout, traumatic arthritis, rubella arthritis and acute synovitis, rheumatoid spondylitis, osteoarthritis, gouty arthritis, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption disease, osteoporosis, restenosis, cardiac and renal reperfusion injury, congestive heart failure, chronic renal failure, glomerulonephritis, angiogenesis & related processes, thrombosis, diabetes, graft vs. host reaction, allograft rejection, inflammatory bowel disease, Crohn's disease, incerative colitis, multiple sclerosis, muscle degeneration, eczema, contact dermititis, psoriasis, sunburn, or conjunctivitis.

14. The method according to claim 12 wherein $R_1$ is a 4-pyrimidinyl group substituted by Y.

15. The method according to claim 14 wherein $X_1$ is oxygen, and $R_a$ is an optionally substituted aryl or an optionally substituted arylalkyl.

16. The method according to claim 14 wherein Ra' is optionally substituted $C_{1-4}$ alkyl.

17. The method according to claim 12 wherein $R_2$ is hydrogen, optionally substituted $C_{1-10}$ alkyl group, an optionally substituted aryl, an optionally substituted heterocyclyl, or an optionally substituted heterocyclyl$C_{1-10}$ alkyl.

18. The method according to claim 12 wherein Q is an optionally substitued phenyl.

19. The method according to claim 18 wherein Q is phenyl substitued independently by halogen, halosubstituted alkyl, or $(CR_{10}R_{20})_nY_2$ and $Y_2$ is $OR_8$, $S(O)_m R_{11}$, $SR_8$, $S(O)_m NR_8R_9$, or $NR_8R_9$.

20. The method according to claim 12 wherein $R_4$ is optionally substituted phenyl, naphth-1-yl or naphth-2-yl wherein the 4-phenyl, 4-naphth-1-yl or 5-naphth-2-yl moiety are substituted by one or two substituents each independently selected from halogen, $SR_5$, $SOR_5$, $OR_{36}$, or $(CR_{10}R_{20})_m NR_{10}R_{20}$, and for other positions of substitution on these rings the substitution is halogen, $S(O)_m R_8$, $OR_8$, $(CR_{10}R_{20})_m NR_{16}R_{26}$, $NR_{10}C(Z)R_8$ and $NR_{10}S(O)_m R_{11}$.

21. The method according to 20 wherein the substituent in the 4-position for phenyl and naphth-1-yl and on the 5-position in naphth-2-yl is fluoro, chloro, $SR_5$ or $SOR_5$.

22. The method according to claim 12, wherein the compound of Formula (I) is:

2-[(4-N,N-Dimethyl)aminomethylphenyl]-4-(4-fluorophenyl)-5-(2-phenoxy-4-pyrimidinyl)imidazole;

(+/−) 2-(4-Methylsulfinylphenyl]-4-(4-fluorophenyl)-5-(2-phenoxy4-pyrimidinyl)imidazole;

2-(4-Methylthlophenyl]-4-(4-fluorophenyl)-5-(2-phenoxy-4-pyrimidinyl)imidazole;

or a pharmaceutically acceptable salt thereof.

* * * * *